(12) United States Patent
Nara

(10) Patent No.: US 11,644,661 B2
(45) Date of Patent: May 9, 2023

(54) MEDICAL IMAGE PICKUP APPARATUS

(71) Applicant: OLYMPUS CORPORATION, Tokyo (JP)

(72) Inventor: Tetsuro Nara, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 754 days.

(21) Appl. No.: 16/444,017

(22) Filed: Jun. 18, 2019

(65) Prior Publication Data

US 2019/0357760 A1   Nov. 28, 2019

Related U.S. Application Data

(63) Continuation of application No. PCT/JP2017/031574, filed on Sep. 1, 2017.

(30) Foreign Application Priority Data

Dec. 19, 2016   (JP) .............................. JP2016-245634

(51) Int. Cl.
| | |
|---|---|
| *G02B 23/24* | (2006.01) |
| *A61B 1/045* | (2006.01) |
| *A61B 1/05* | (2006.01) |
| *H04N 5/225* | (2006.01) |
| *A61B 1/06* | (2006.01) |
| *A61B 1/00* | (2006.01) |

(52) U.S. Cl.
CPC .......... *G02B 23/2484* (2013.01); *A61B 1/045* (2013.01); *A61B 1/05* (2013.01);
(Continued)

(58) Field of Classification Search
CPC ....... A61B 1/05; A61B 1/045; A61B 1/00009; A61B 1/0676; A61B 1/00105;
(Continued)

(56) References Cited

U.S. PATENT DOCUMENTS

2008/0300463 A1\* 12/2008 Navok ..................... A61B 1/07
                                                                            600/176
2012/0202385 A1   8/2012 Miyagi et al.
(Continued)

FOREIGN PATENT DOCUMENTS

| EP | 2478825 A1 | 7/2012 |
|---|---|---|
| JP | 2008-212363 A | 9/2008 |
| JP | 2013-056003 A | 3/2013 |

(Continued)

OTHER PUBLICATIONS

International Search Report dated Nov. 21, 2017 issued in PCT/JP2017/031574.

*Primary Examiner* — Aaron B Fairchild
*Assistant Examiner* — Christen A. Sharpless
(74) *Attorney, Agent, or Firm* — Scully, Scott, Murphy & Presser, P.C.

(57) ABSTRACT

A camera head includes an airtight case which includes an image pickup unit having an image pickup device and the like as a heat source in an inner portion and includes a partition wall to secure air-tightness with respect to an outside of the airtight case, a heat transfer sheet which connects the heat source and an inner surface of the partition wall to transfer heat generated at the heat source to the partition wall, a heat sink arranged on an outer side of the partition wall of the airtight case, and a spring member which is interposed between an outer surface corresponding to the inner surface of the partition wall of the airtight case connected to the heat transfer sheet and the heat sink to transfer heat from the outer surface of the partition wall to the heat sink.

20 Claims, 9 Drawing Sheets

(52) U.S. Cl.
CPC ........ *H04N 5/2253* (2013.01); *A61B 1/00009* (2013.01); *A61B 1/0676* (2013.01); *H04N 2005/2255* (2013.01)

(58) Field of Classification Search
CPC . A61B 1/00124; A61B 1/00188; A61B 1/128; A61B 1/0669; A61B 1/07; A61B 1/00066; A61B 1/042; G02B 23/2484; H04N 5/2253; H04N 2005/2255; H04N 5/22521
USPC .......................................................... 600/112
See application file for complete search history.

(56) References Cited

U.S. PATENT DOCUMENTS

| | | | |
|---|---|---|---|
| 2016/0278620 A1 | 9/2016 | Kawayoke | |
| 2016/0338580 A1* | 11/2016 | Amano | ................. A61B 1/051 |
| 2018/0031797 A1* | 2/2018 | Kobayashi | ............... G02B 7/08 |
| 2019/0117200 A1* | 4/2019 | Morimoto | .............. A61B 8/546 |

FOREIGN PATENT DOCUMENTS

| | | | |
|---|---|---|---|
| JP | 2013056003 A | * | 3/2013 |
| JP | 2014-188210 A | | 10/2014 |
| JP | 2014188210 A | * | 10/2014 |
| JP | 2014228797 A | * | 12/2014 |
| JP | 2015-107218 A | | 6/2015 |
| JP | 2016-214662 A | | 12/2016 |
| JP | 6184655 B1 | | 8/2017 |
| WO | WO 2011/052408 A1 | | 5/2011 |
| WO | WO 2015/083416 A1 | | 6/2015 |
| WO | WO 2017/134884 A1 | | 8/2017 |

\* cited by examiner

MEDICAL IMAGE PICKUP APPARATUS

CROSS REFERENCE TO RELATED APPLICATION

This application is a continuation application of PCT/JP2017/031574 filed on Sep. 1, 2017 and claims benefit of Japanese Application No. 2016-245634 filed in Japan on Dec. 19, 2016, the entire contents of which are incorporated herein by this reference.

BACKGROUND OF THE INVENTION

1. Field of the Invention

The present invention relates to a medical image pickup apparatus in which a heat source such as an image pickup portion is sealed in an inner portion of an airtight case.

2. Description of the Related Art

Conventionally, a medical image pickup apparatus which is freely attachable to an eye piece of an endoscope has been known in a medical field. The medical image pickup apparatus has an image pickup portion configured by a solid-state image pickup device and various electronic parts, and can pick up an object image emitted from the eye piece.

Also, the medical image pickup apparatus after such image pickup is executed is subjected to cleaning, disinfection and sterilization. As a sterilization method, a sterilization process under high temperature and high pressure steam (hereinafter referred to as autoclave processing) has been known, and to make the medical image pickup apparatus compatible with such autoclave processing, airtight sealing of the image pickup portion is needed.

For example, Japanese Patent Application Laid-Open Publication No. 2013-56003 discloses a technology in which an airtight case made of metal is provided on an exterior portion formed of resin, and by sealing an image pickup portion in the airtight case, the image pickup portion is protected from high temperature and high pressure steam intruding into the exterior portion. Additionally, the airtight case should be made of metal, because resin is difficult to achieve an airtight structure, and moreover, laser welding is required in sealing the airtight case and the like.

SUMMARY OF THE INVENTION

According to one aspect of the present invention, there is provided a medical image pickup apparatus including: an airtight case which includes a heat source in an inner portion and includes a partition wall to secure air-tightness with respect to an outside of the airtight case; a first heat transfer member which connects the heat source and an inner surface of the partition wall to conduct heat generated at the heat source to the partition wall; a heat dissipation member arranged on an outer side of the partition wall; and a second heat transfer member which is interposed between an outer surface corresponding to the inner surface of the partition wall connected to the first heat transfer member and the heat dissipation member to conduct heat from the outer surface of the partition wall to the heat dissipation member.

DETAILED DESCRIPTION OF THE PREFERRED EMBODIMENT

Figure 2:
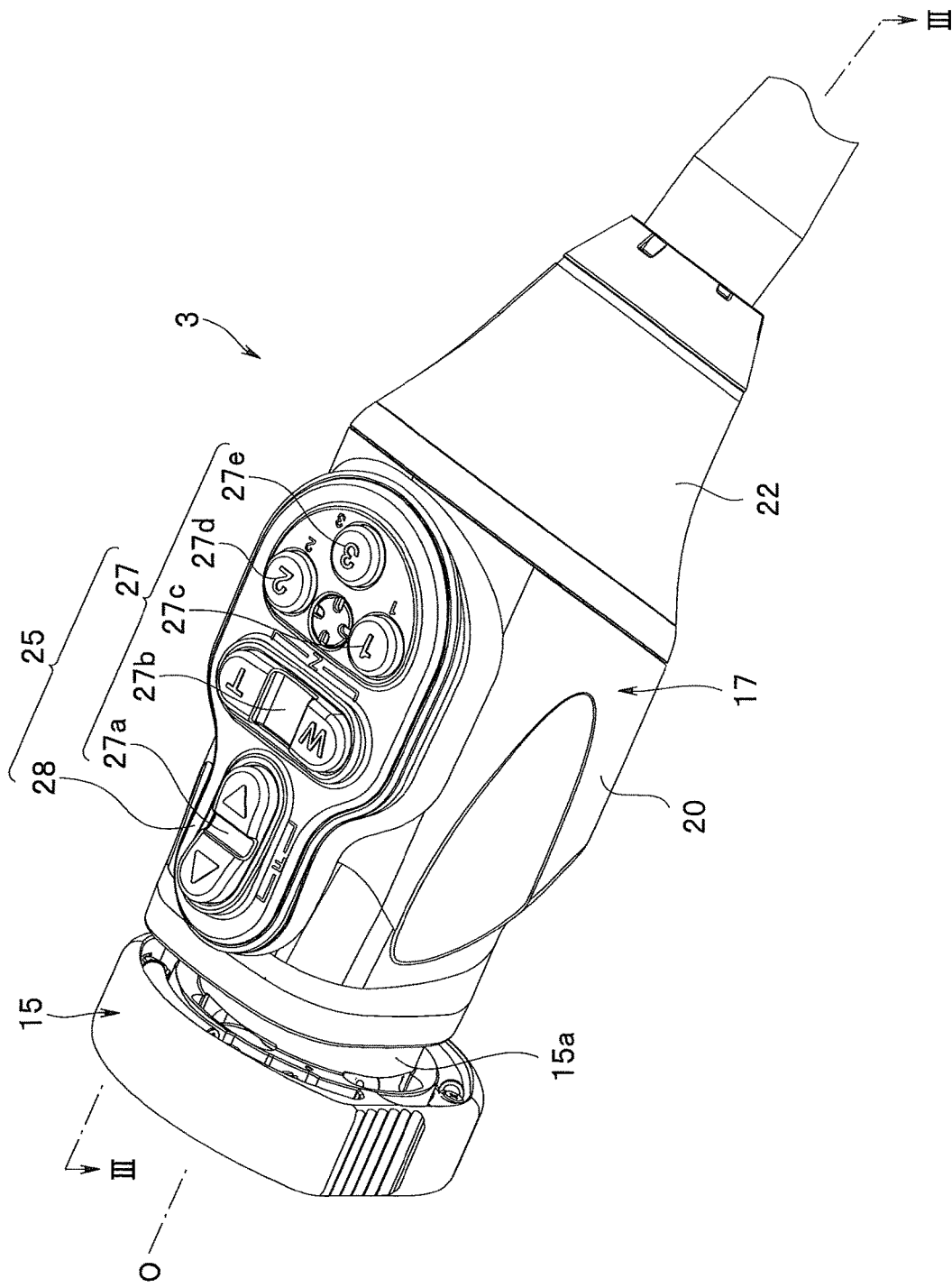
FIG. 2 is a perspective view showing an appearance of a camera head.
Figure 3:
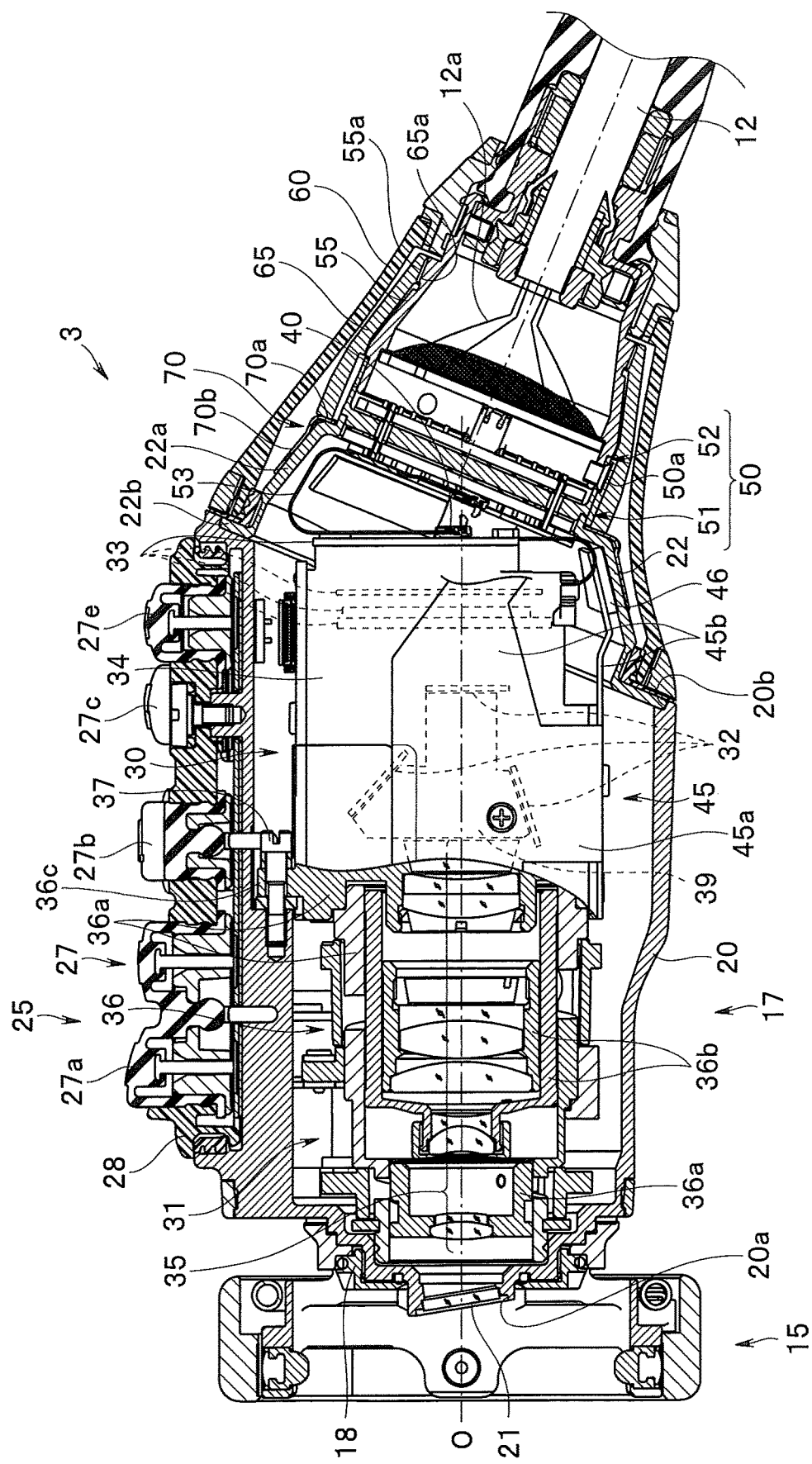
FIG. 3 is a cross-sectional view of a main part along the line of FIG. 2.
Figure 4:
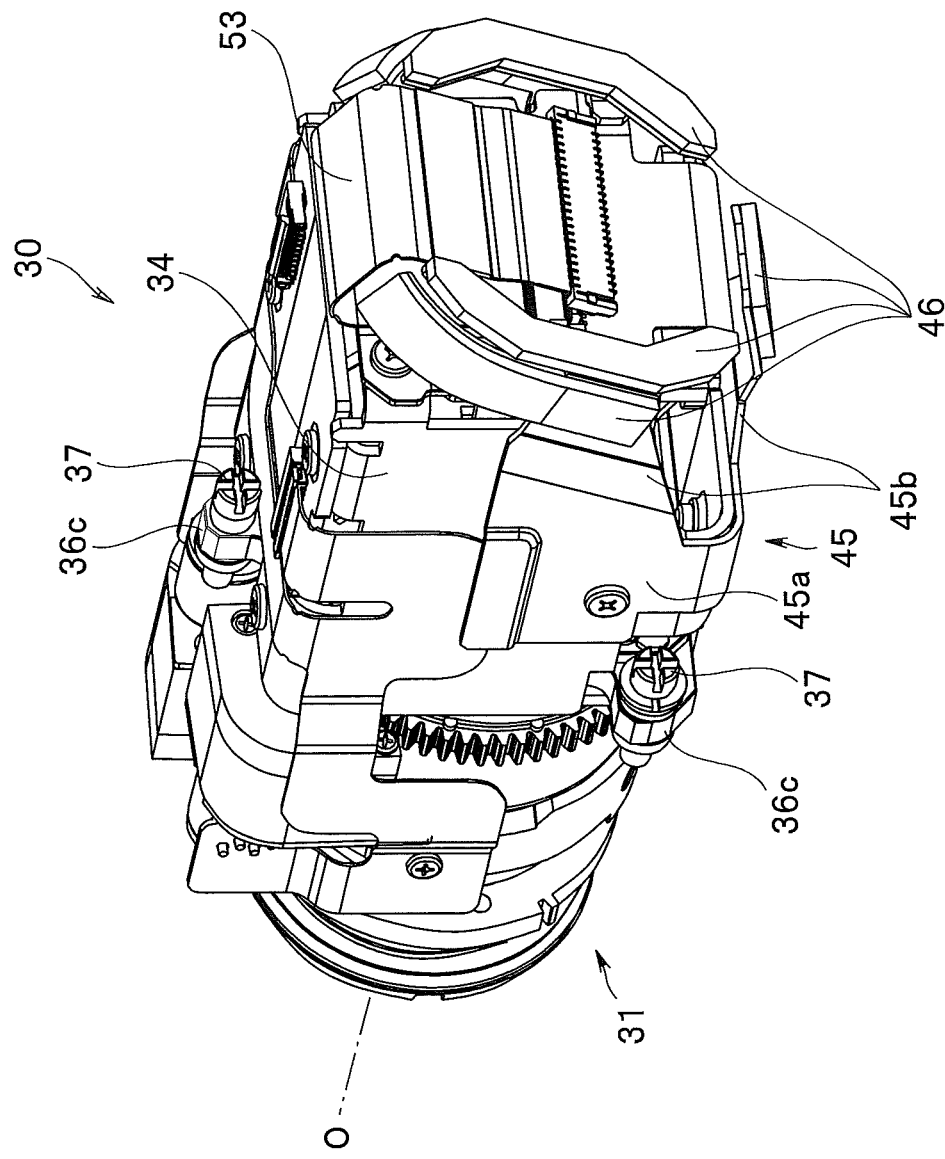
FIG. 4 is a perspective view showing an image pickup unit.
Figure 5:
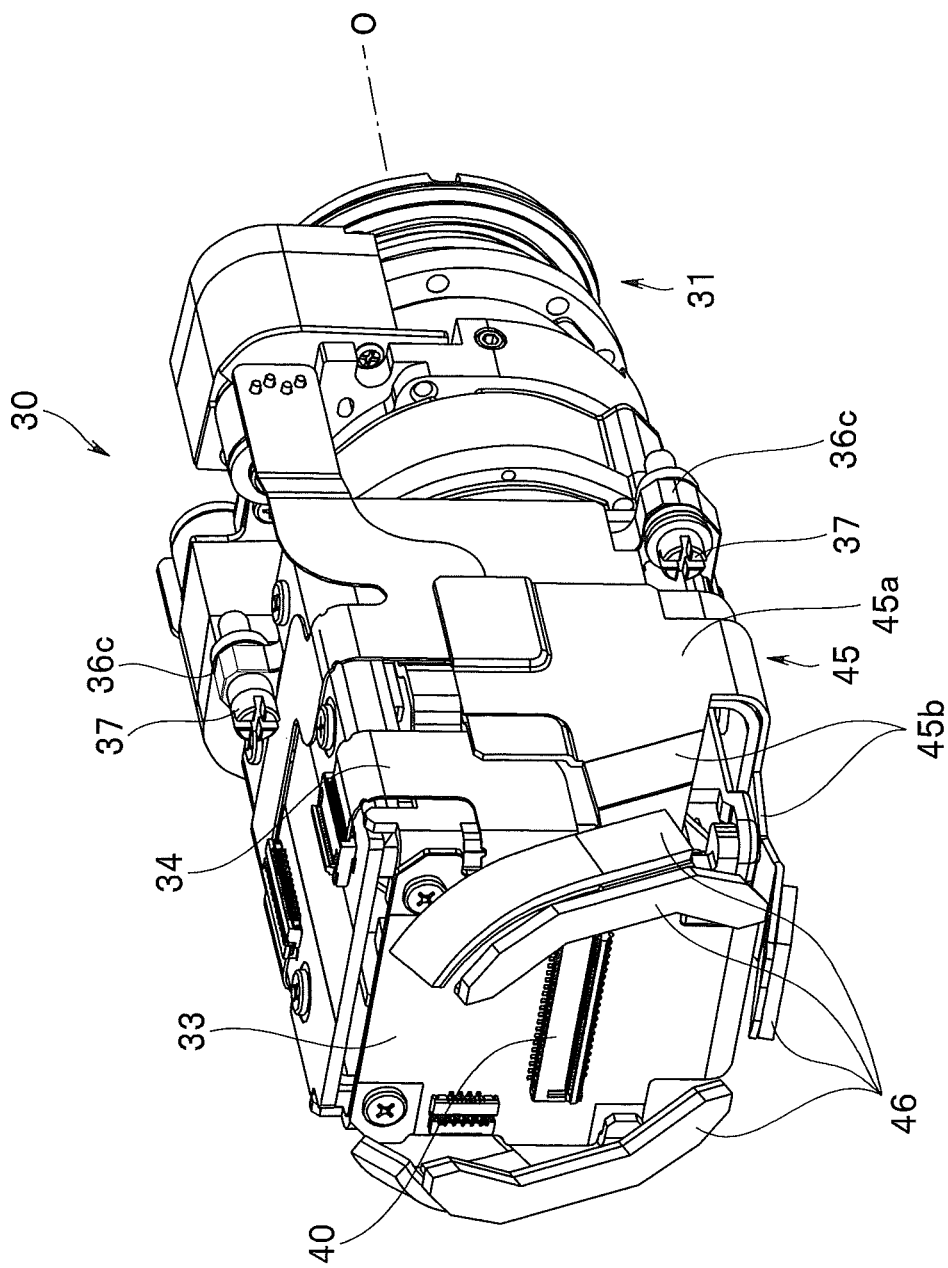
FIG. 5 is a perspective view of the image pickup unit shown from a point different from FIG. 4.
Figure 6:
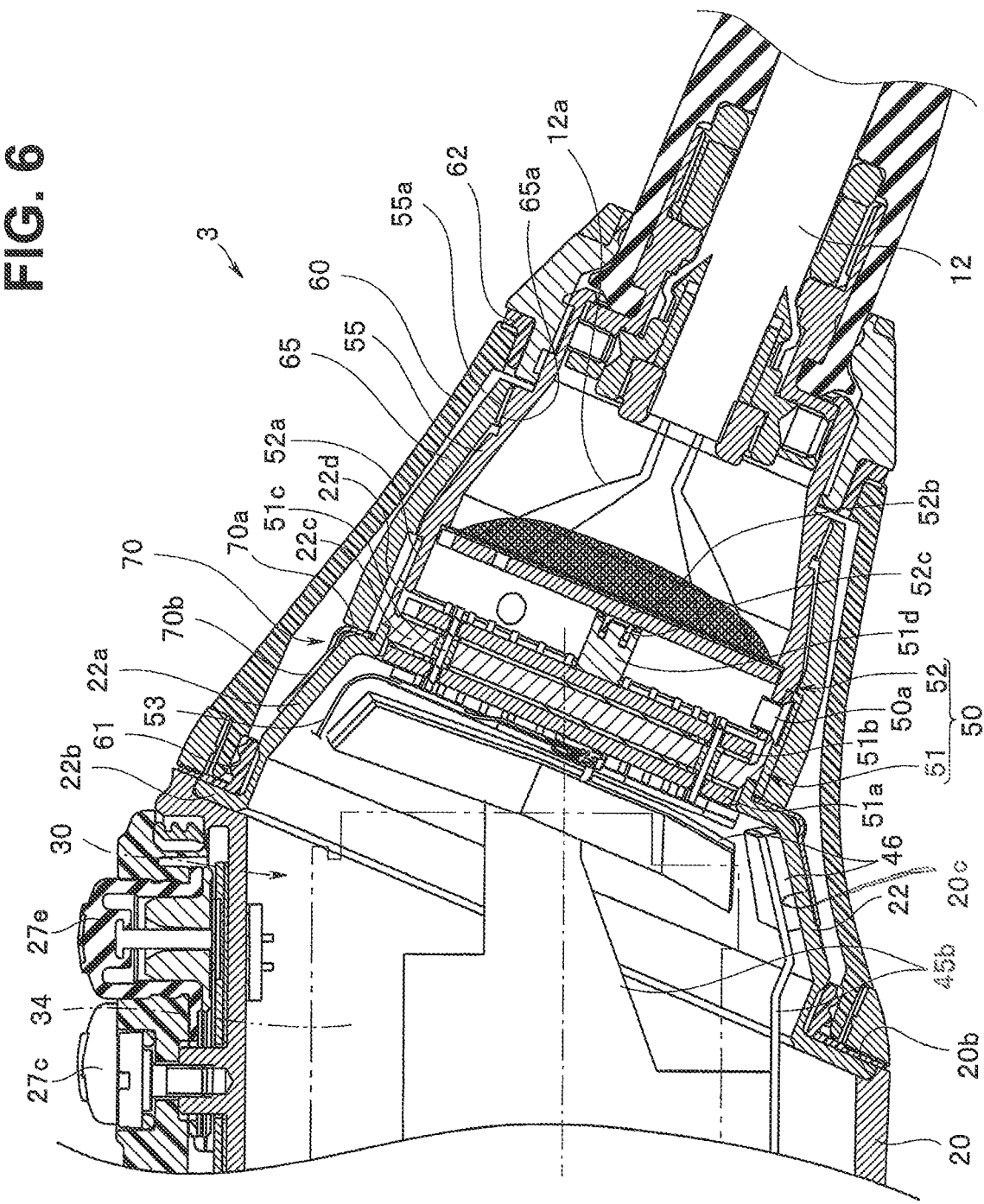
FIG. 6 is a cross-sectional view showing a main part of the camera head with enlargement.
Figure 7:
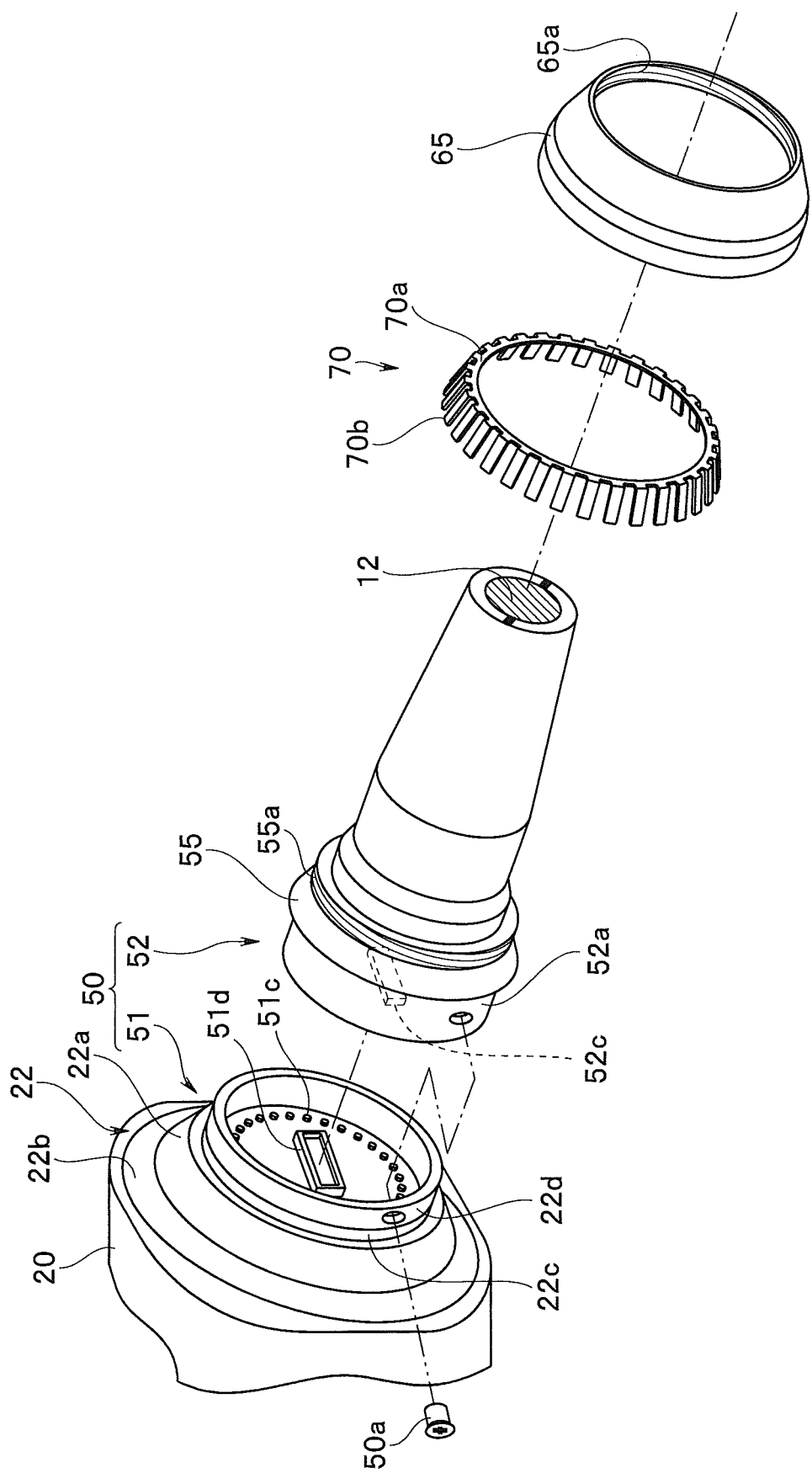
FIG. 7 is an exploded perspective view of a connector portion and a heat dissipation mechanism.
Figure 8:
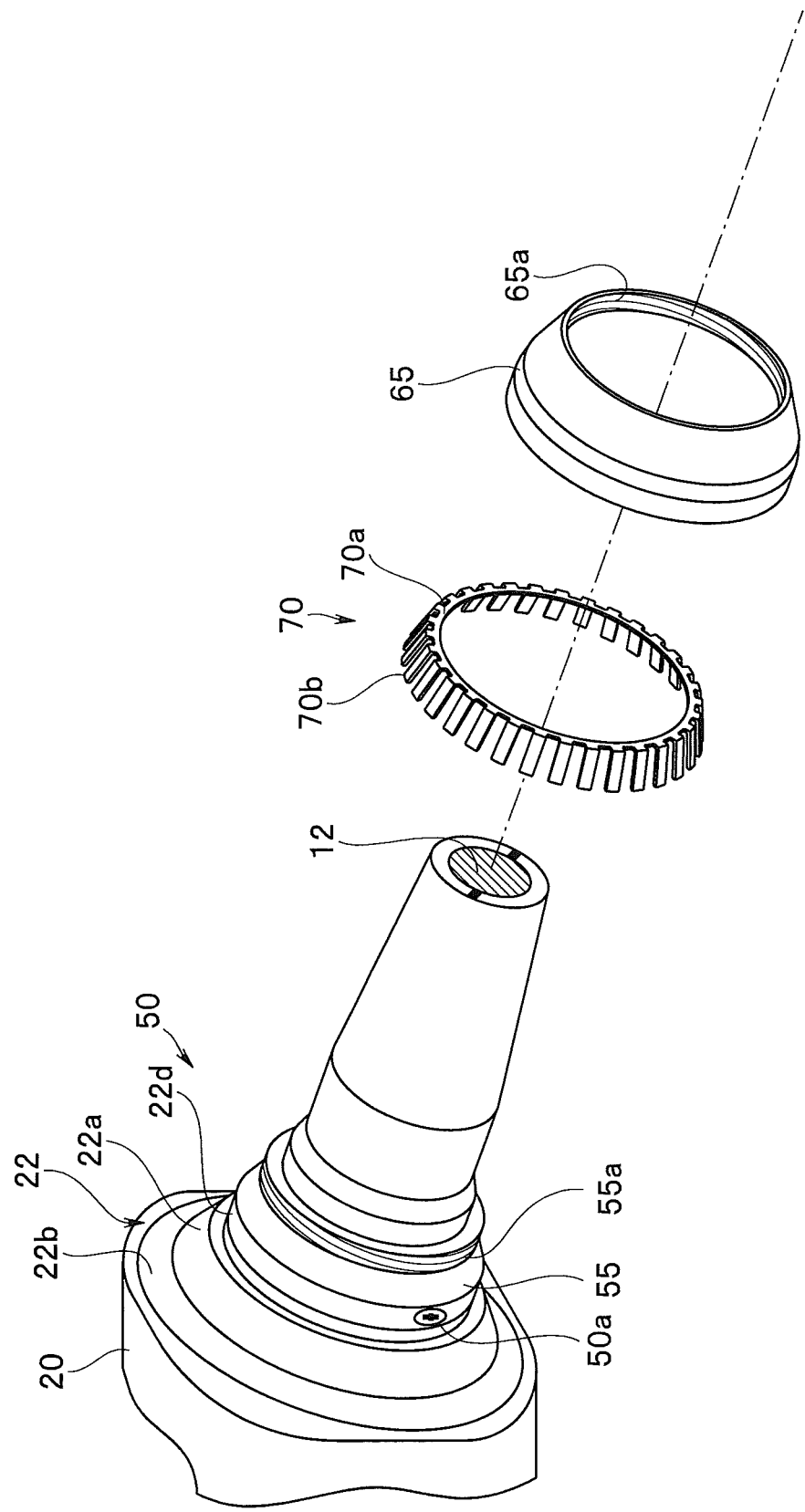
FIG. 8 is an exploded perspective view of the heat dissipation mechanism.
Figure 9:
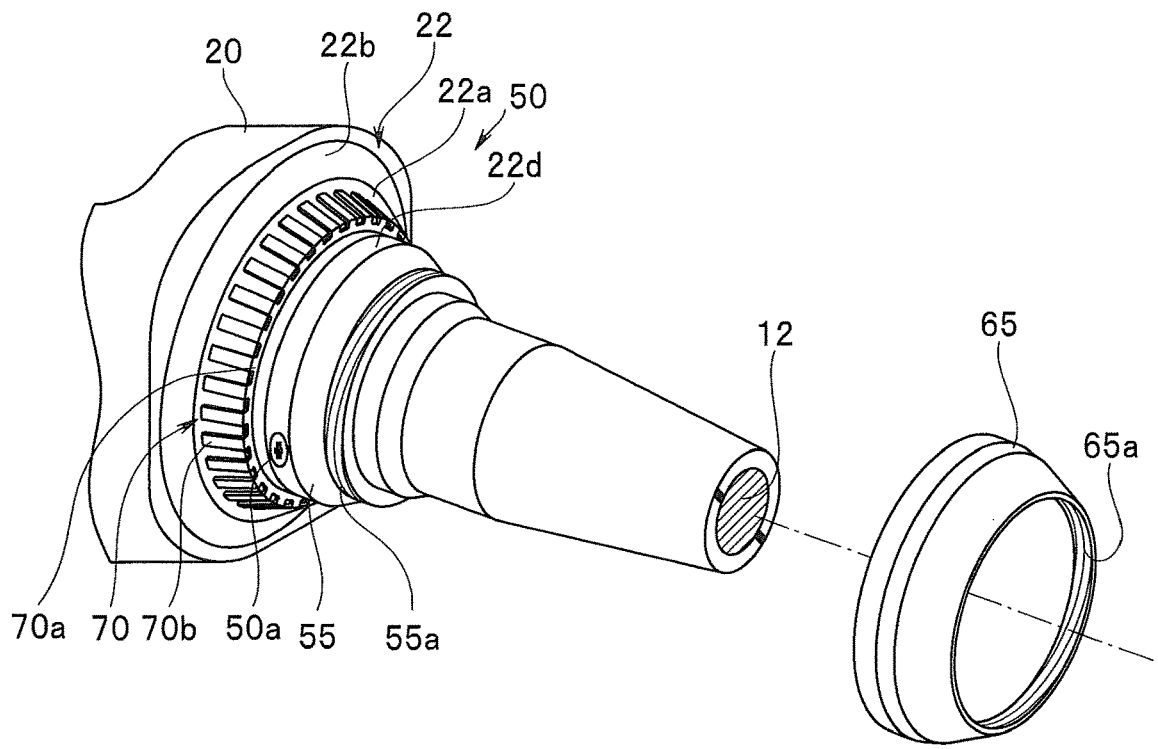
FIG. 9 is a perspective view of the heat dissipation mechanism with a heat sink removed.
Figure 10:
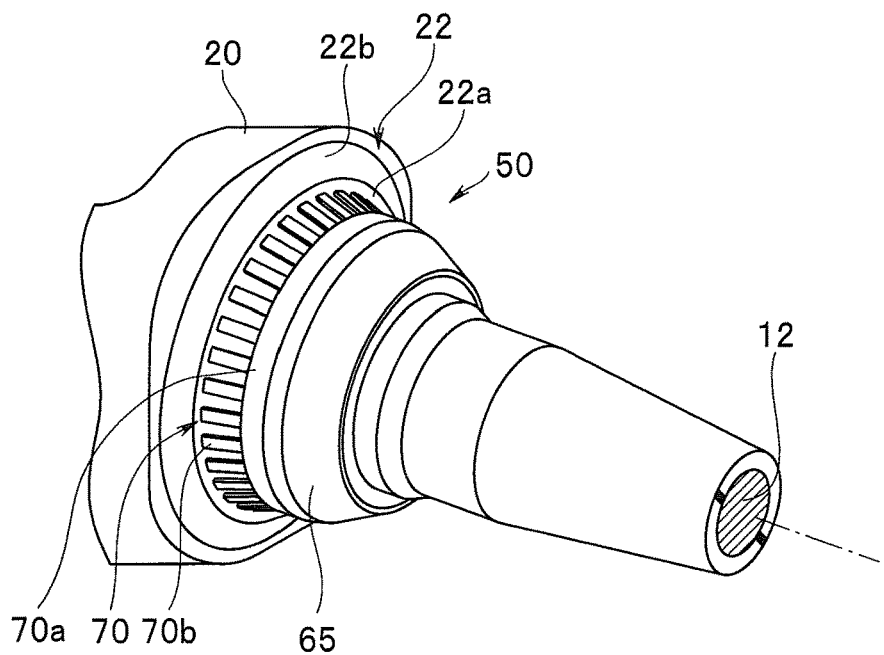
FIG. 10 is a perspective view of the heat dissipation mechanism.

Hereinafter, a form of the present invention will be explained with reference to the drawings. The drawings relate to one embodiment according to the present invention, in which FIG. 1 is a schematic configuration diagram of an endoscope system including a medical image pickup apparatus, FIG. 2 is a perspective view showing an appearance of a camera head, FIG. 3 is a cross-sectional view of a main part along the line of FIG. 2, FIG. 4 is a perspective view showing an image pickup unit, FIG. 5 is a perspective view of the image pickup unit shown from a point different from FIG. 4, FIG. 6 is a cross-sectional view showing a main part of the camera head with enlargement, FIG. 7 is an exploded perspective view of a connector portion and a heat dissipation mechanism, FIG. 8 is an exploded perspective view of the heat dissipation mechanism, FIG. 9 is a perspective view of the heat dissipation mechanism with a heat sink removed; and FIG. 10 is a perspective view of the heat dissipation mechanism.

Figure 1:
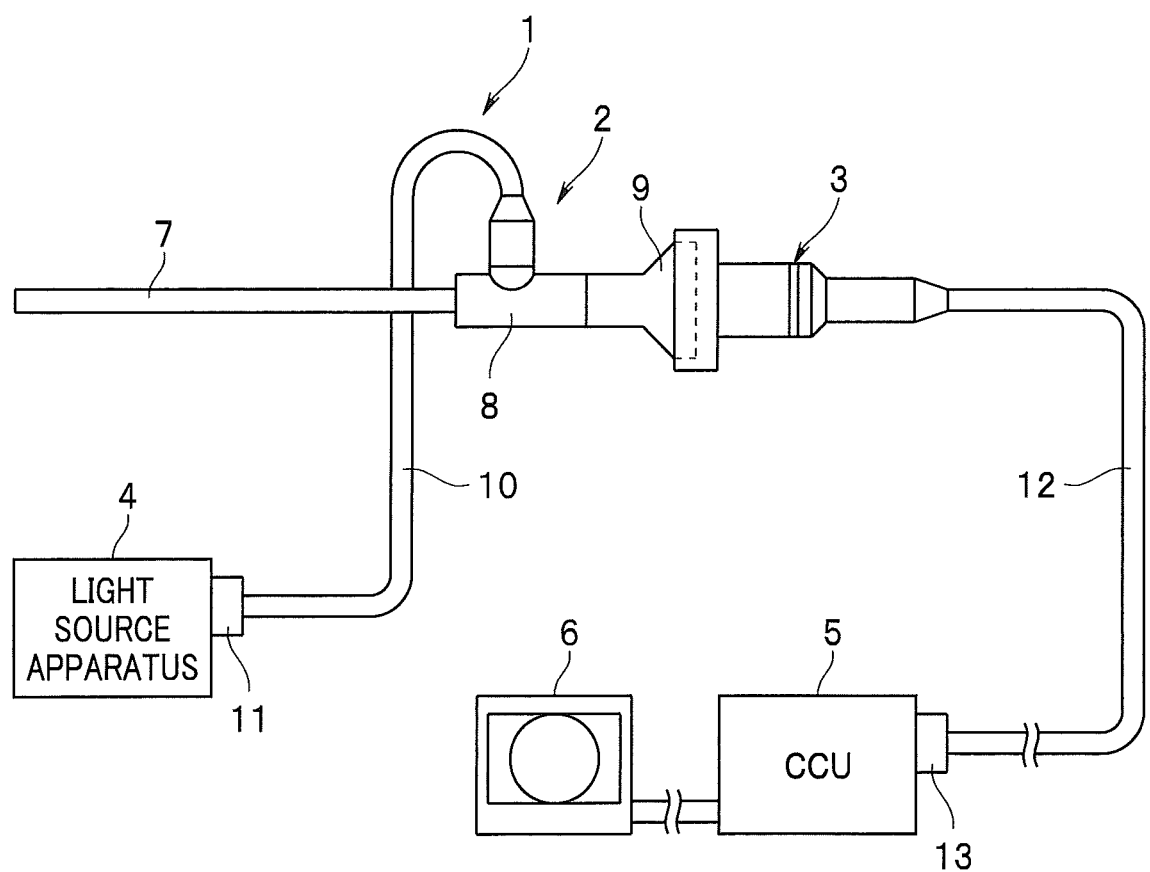
FIG. 1 is a schematic configuration diagram of an endoscope system including a medical image pickup apparatus.

As shown in FIG. 1, an endoscope system 1 includes an endoscope 2, a camera head 3 as a medical image pickup apparatus which is connectable to the endoscope 2 and a light source apparatus 4 which supplies an illumination light to the endoscope 2.

The endoscope system 1 includes a camera control unit (CCU) 5 which executes signal processing and the like on an image pickup signal from the camera head 3 and a monitor 6 which displays a video signal outputted from the CCU 5.

The endoscope 2 includes a main part configured by an elongated insertion portion 7, a grasping portion 8 having a larger diameter than a diameter of the insertion portion 7 provided at a proximal end side of the insertion portion 7 and an eye piece 9 provided at a proximal end of the grasping portion 8.

One end of a light guide cable 10 is connected to a side portion of the grasping portion 8 of the endoscope 2 via a pipe sleeve, and the other end of the light guide cable 10 is connected to the light source apparatus 4 freely detachably via a connector 11. Thus, a light emitted from a not shown lamp in the light source apparatus 4 is supplied to the endoscope 2 via the light guide cable 10 and irradiated to the inside of a subject from a not shown illumination window provided at a distal end of the insertion portion 7.

An image of the inside of the subject illuminated by an illumination light forms an image on a not shown objective optical system provided at the distal end of the insertion portion 7, and the formed optical image enters a lens provided in the eye piece 9 via a not shown relay lens or the like provided in the insertion portion 7. This allows an operator to observe the optical image via the eye piece 9.

As described above, the camera head 3 is freely connected to the eye piece 9, and an extending end of a camera cable 12 extending from the camera head 3 is freely attachable to the CCU 5 via a connector 13.

The CCU 5 generates an image signal based on the image pickup signal transmitted from the camera head 3 via the camera cable 12, and causes the monitor 6 to display the image of the inside of the subject as an endoscope image.

Next, with reference to FIGS. 2 to 10, a concrete configuration of the camera head 3 will be explained.

As shown in FIGS. 2 and 3, the camera head 3 is configured to include a coupler portion 15 and an airtight case 17 connected to the coupler portion 15.

The coupler portion 15 is configured by a substantially cylindrical member freely attachable to the eye piece 9 of the endoscope 2.

Also, a fitting portion 15a to be fitted to an outer periphery on a distal end side of the airtight case 17 is provided at a proximal end side of the coupler portion 15. Moreover, after the fitting portion 15a is fitted to the outer periphery of the airtight case 17, a fitting condition is maintained by a substantially ring-shaped fixing screw 18, so that the coupler portion 15 is connected to the airtight case 17.

The airtight case 17 is a case also used as an exterior portion of the camera head 3, and has a function as a grasping portion such that an operator can grasp the grasping portion in operating the camera head 3 and the like. The airtight case 17 is configured to include a substantially cylindrical main case 20 made of metal in which both ends in a direction of a longitudinal axis O are opened, a glass-made observation window 21 for airtight sealing a distal end opening 20a of the main case 20 and a rear case 22 made of metal for airtight sealing a proximal end opening 20b of the main case 20.

Here, as metal which forms the main case 20 and the rear case 22, metal suitable for soldering and airtight welding (laser welding or the like) is preferably used. In this embodiment, lightweight titanium alloy is preferably adopted. Additionally, as other metal which forms the main case 20 and the rear case 22, titanium, stainless steel or the like may be adopted.

As shown in FIGS. 2 and 3, on one side surface on an outer periphery of the main case 20, a switch unit 25 used for an image pickup operation of the image of the inside of the subject is fixed in a direction of the longitudinal axis O of the camera head 3.

The switch unit 25 is configured to include switch buttons 27 covered by a rubber cover or the like and a switch button frame 28 which attaches the switch buttons 27 to the main case 20 in a watertight manner.

The switch buttons 27 include, for example, a focus adjustment button 27a, a zoom button 27b and custom buttons 27c, 27d and 27e which are assigned functions such as brightness adjustment, color adjustment and release.

Also, as shown in FIG. 3, an image pickup unit 30 is provided in the main case 20.

The image pickup unit 30 is configured to include an image pickup optical system 31, a plurality of (for example, three) image pickup devices 32 as a heat source, a plurality of element substrates 33 to which various electronic parts as a heat source are implemented and a retaining frame 34 which integrally retains these image pickup devices 32 and the element substrates 33 to a proximal end side of the image pickup optical system 31.

The image pickup optical system 31 is configured to include a plurality of lenses 35 and a lens frame 36 which retains the plurality of lenses 35 in a direction of an optical axis (that is, in this embodiment, a direction corresponding to a direction of the longitudinal axis O of the main case 20).

Here, the lens frame 36 is configured to include a plurality of fixing frames 36a and a movable frame 36b which can perform advancing or retracting movement in the optical axis direction by a not shown actuator. Moreover, each lens 35 retained by the movable frame 36b performs advancing or retracting movement in the optical axis direction with respect to each lens 35 retained by each fixing frame 36a, so that the image pickup optical system 31 can perform a focus adjustment function and a zoom function.

A plurality of (for example, three) fixing projections 36c are provided to the fixing frame 36a positioned at the most proximal end of the image pickup optical system 31, for example. A screw 37 which penetrates in the direction of the longitudinal axis O is provided to each fixing projection 36c, and the screws 37 are threaded into a stepped portion formed in the main case 20. Thus, the image pickup optical system 31 is fixed in the main case 20, and the retaining frame 34 continuously provided from the image pickup optical system 31 is retained basically in a non-contacting state to the main case 20.

Each image pickup device 32 is optically connected to the image pickup optical system 31 via a prism 39 in an inner portion of the retaining frame 34, so that an optical image formed by the image pickup optical system 31 can be picked up.

Each element substrate 33 is arranged at a proximal end side relative to each image pickup device 32 in the inner portion of the retaining frame 34. Various electronic parts configuring a driving circuit and the like of each image pickup device 32 are implemented to each element substrate 33. Further, as shown in FIGS. 3 and 4, a connector portion 40 which is electrically connected to each driving circuit and the like is implemented to the element substrate 33 positioned at a proximal end of the retaining frame 34.

The retaining frame 34 is configured by a substantially box-shaped frame member made of aluminum alloy or the like with excellent thermal conductivity.

As shown in FIGS. 3 to 5, a heat exchanger plate 45 made of aluminum alloy with excellent thermal conductivity or copper or the like is provided on an outer surface of the retaining frame 34.

The heat exchanger plate 45 is configured to include a heat exchanger plate main body 45a which is contacted and fixed to the retaining frame 34 by screw fastening or the like and a plurality of (for example, two or three) arm portions 45a extending from the heat exchanger plate main body 45a toward the proximal end opening of the main case 20. Further, a heat transfer sheet 46 which is a sheet-like heat transfer member made of an elastic body (or gel) with high thermal conductivity is fixedly mounted to an extending end of each arm portion 45b, respectively.

As shown in FIG. 3, the observation window 21 is arranged such that an outer peripheral portion is in contact along the distal end opening 20a of the main case 20. The outer peripheral portion of the observation window 21 is metalized. Moreover, the metalized outer peripheral portion is air-tightly fixed to the main case 20 by soldering or the like, so that the observation window 21 air-tightly seals the distal end opening 20a of the main case 20.

The image pickup optical system 31 of the image pickup unit 30 faces the observation window 21 which air-tightly seals the distal end opening 20a of the main case 20 as described above. Thus, the camera head 3 can pick up an image of an object emitted from the eye piece 9 when the coupler portion 15 is mounted to the eye piece 9.

As shown in FIGS. 3 and 6, the rear case 22 is configured by a member of substantially a hat shape in cross section including an annular tapered wall portion 22a which protrudes while reducing a diameter toward a proximal end side in a state of being inclined at a predetermined angle to the longitudinal axis O of the main case 20, a flange portion 22b circumferentially provided at a distal end of the tapered wall portion 22a, a connector portion main body 22c arranged at a proximal end (protruding end) of the tapered wall portion 22a. Here, the connector portion main body 22c is configured by a substantially disc-like member in which a substantially ring-like first fitting portion 22d is integrally formed at a proximal end side, which configures a connector portion (first connector portion 51) of a hermetic connector 50 which will be described later. An outer peripheral portion of the connector portion main body 22c is fixed to the tapered wall portion 22a by laser welding or the like. Thus, the proximal end of the tapered wall portion 22a (proximal end of the rear case 22) is air-tightly closed.

The rear case 22 is arranged such that the flange portion 22b is in contact along the proximal end opening 20b of the main case 20. Moreover, since the flange portion 22b is air-tightly fixed to the main case 20 by laser welding or the like, the rear case 22 air-tightly seals the proximal end opening 20b of the main case 20.

The heat transfer sheet 46 fixedly provided at each arm portion 45b of the heat exchanger plate 45 is in thermally conductive contact with an inner surface of the rear case 22 which air-tightly seals the proximal end opening 20b of the main case 20 as described above.

In other words, in this embodiment, the heat transfer sheet 46 has a function as a first heat transfer member, and is elastically contacted with pressure to the inner surface of the rear case 22 (see FIGS. 3 and 6). More specifically, each heat transfer sheet 46 is supported to be arranged substantially annually by each arm portion 45b (see FIGS. 4 and 5) to be elastically contacted with pressure to an inner peripheral surface of the tapered wall portion 22a formed at the rear case 22.

Thus, the image pickup unit 30 including the heat source and the inner surface of the rear case 22 configuring a part of a partition wall of the airtight case 17 are thermally connected, so that heat generated at the image pickup unit 30 can be conducted to the rear case 22.

Also, the first connector portion 51 configuring the hermetic connector 50 is provided at a proximal end portion (more specifically, a protruding end of the tapered wall portion 22a) of the rear case 22.

As shown in FIGS. 6 and 7, in this embodiment, the first connector portion 51 is configured to include an inner substrate 51a fixed at an inner surface side of the connector portion main body 22c (inner surface side of the rear case 22) by soldering, an outer substrate 51b fixed at an outer surface side of the connector main body 22c (outer surface side of the rear case 22) by soldering, a plurality of pins 51c which penetrate through the inside and the outside of the connector portion main body 22c air-tightly to electrically connect the inner substrate 51a and the outer substrate 51b and a first connector terminal portion 51d implemented to the outer substrate 51b. At the inner surface side of the rear case 22, one end of a flexible substrate 53 is electrically connected to each pin 51c via the inner substrate 51a, while the other end of the flexible substrate 53 is electrically connected to the connector portion 40 implemented to the element substrate 33 of the image pickup unit 30. Also, at the outer surface side of the rear case 22, the first connector terminal portion 51d is electrically connected to each pin 51c via the outer substrate 51b.

On the other hand, as shown in FIGS. 6 to 9 for example, at the outside of the airtight case 17, a cable fixing frame 55 fixed to a distal end portion of the camera cable 12 is connected to the proximal end portion of the rear case 22 to be freely detachable.

More specifically, a second connector portion 52 configuring the hermetic connector 50 is provided at a distal end portion of the cable fixing frame 55. The second connector portion 52 includes a second fitting portion 52a integrally formed at a distal end of the cable fixing frame 55. The second fitting portion 52a has a shape which is freely fitted to an inner periphery of the first fitting portion 22d, and a substrate 52b is provided at an inner portion of the second fitting portion 52a. Also, a second connector terminal portion 52c corresponding to the first connector terminal portion 51d is implemented on an outer surface side of the substrate 52, while each signal line 12a branched from the camera cable 12 is electrically connected to an inner surface side of the substrate 52b.

Moreover, when the second connector portion 52 is fitted to the first connector portion 51, the cable fixing frame 55 is connected to the proximal end portion of the rear case 22, and each signal line 12a of the camera cable 12 is electrically connected to the element substrate 33 of the image pickup unit 30 via the flexible substrate 53. For example, as shown in FIG. 8, the first connector portion 51 and the second connector portion 52 after fitting are held in place by a screw 50a which penetrates through side portions of the first fitting portion 22d and the second fitting portion 52a.

Here, the cable fixing frame 55 is preferably formed of a material with higher thermal conductivity than thermal conductivity of the airtight case 17. In this embodiment, the cable fixing frame 55 is formed of stainless steel with higher thermal conductivity than thermal conductivity of titanium alloy.

Also, an outer periphery of the rear case 22 and the cable fixing frame 55 is covered by a resin-made rear external cover 60. In other words, in the airtight case 17 in this embodiment, only a portion at a proximal end side (only the rear case 22) is covered by the rear external cover 60. Seal rings 61, 62 are respectively interposed at a proximal end portion and a distal end portion of the rear external cover 60, and by these seal rings 61, 62, water-tightness of an inner portion of the rear external cover 60 is maintained.

For example, as shown in FIG. 3 and FIGS. 6 to 10, a heat sink 65 as a heat dissipation member is arranged at the inside of the rear external cover 60 as well as the outer side of the rear case 22.

More specifically, the heat sink 65 in this embodiment is fixedly mounted to an outer peripheral portion of the cable fixing frame 55, so that heat can be transmitted to a conductor in an inner portion of the camera cable 12 via the cable fixing frame 55.

More specifically, as shown in FIGS. 6 to 9 for example, a male screw portion 55a is formed on an outer peripheral portion at a proximal end side of the cable fixing frame 55. On the other hand, a female screw portion 65a is formed on an inner peripheral surface at a proximal end side of the heat sink 65. Moreover, when the female screw portion 65a of the heat sink 65 is threaded into the male screw portion 55a of the cable fixing frame 55, the heat sink 65 is fixedly mounted to the cable fixing frame 55 in a state of allowing thermal conduction.

Here, the heat sink 65 is preferably formed of a material with higher thermal conductivity than thermal conductivity of the airtight case 17. In this embodiment, the heat sink 65 is formed of aluminum alloy with higher thermal conductivity than thermal conductivity of titanium alloy.

Further, a spring member 70 as a second heat transfer member which transfers heat to the heat sink 65 from a corresponding portion 20c of an outer surface of the tapered wall portion 22a which is a part of the partition wall of the airtight case 17 is provided at the inside of the rear external cover 60.

More specifically, the spring member 70 in this embodiment is configured by a metal leaf spring in which a ring portion 70a arranged on an outer peripheral portion of the first connector portion 51 and a plurality of arm portions 70b extending from the ring portion 70a to a distal end side are integrally formed (see FIGS. 7 to 9).

The spring member 70 is retained by the rear case 22 at the outer peripheral portion of the first connector portion 51 when the ring portion 70a is interposed between a proximal end surface (a protruding surface of the tapered wall portion 22a) of the rear case 22 and a distal end surface of the heat sink 65 (see FIGS. 6 and 10). Moreover, when the ring portion 70a is interposed between the tapered wall portion 22a and the heat sink 65 in a pressed state, a distal end portion of each arm portion 70b extended from the ring portion 70a elastically contacts along an outer portion (an outer surface) of the tapered wall portion 22a. Thus, the spring member 70 can transfer heat which is transmitted to the tapered wall portion 22a to the heat sink 65.

As shown in FIG. 6 for example, in each arm portion 70b extending from the ring portion 70a of the spring member 70, an extension length is set such that the distal end portion faces the heat transfer sheet 46 via the tapered wall portion 22a when each arm portion 70b extending from the ring portion 70a of the spring member 70 is pressed to the tapered wall portion 22a by the heat sink 65. In other words, each arm portion 70b is set to contact an outer surface corresponding to an inner surface of the tapered wall portion 22a in contact with each heat transfer sheet 46.

The spring member 70 is preferably formed of a material with sufficiently higher thermal conductivity than thermal conductivity of the airtight case 17. In this embodiment, the spring member 70 is formed of copper with higher thermal conductivity than thermal conductivity of titanium alloy.

According to such embodiment, there is provided the airtight case 17 which includes the image pickup unit 30 having the image pickup device 32 and the like as the heat source in an inner portion and includes the partition wall which secures air-tightness with respect to an outside of the airtight case, the heat transfer sheet 46 which connects the heat source and the inner surface of the partition wall to transfer heat generated by the heat source to the partition wall, the heat sink 65 arranged on an outer side of the partition wall of the airtight case 17 and the spring member 70 which is interposed between the outer surface corresponding to the inner surface of the partition wall of the airtight case 17 connected by the heat transfer sheet 46 and the heat sink 65 to transfer heat to the heat sink 65 from an outer surface of the partition wall. With this configuration, heat generated in an inner portion of the airtight case 17 can be efficiently dissipated without remaining in the airtight case 17.

In other words, also in a case where the airtight case 17 is made of metal which is lightweight and with low thermal conductivity such as titanium alloy to be applicable to laser welding or the like, each heat transfer sheet 46 which transfers heat from the image pickup unit 30 to the airtight case 17 is arranged to face the distal end portion of each arm portion 70b of the spring member 70 for transferring heat of the airtight case 17 to the heat sink 65 via the partition wall of the airtight case 17, so that heat can be transmitted efficiently in a thickness direction of the partition wall of the airtight case 17. Consequently, also in a case where heat dissipation is executed via the partition wall of the airtight case 17 with low thermal conductivity, heat generated in the inner portion of the airtight case 17 can be efficiently dissipated without remaining in the airtight case 17.

Since heat transmitted by the heat transfer sheet 46 can be efficiently transmitted to the spring member 70 without remaining in the airtight case 17, heat dissipation at a circumference of a portion in contact with the heat transfer sheet 46 in the airtight case 17 can be accurately prevented. Accordingly, also in a case where the airtight case 17 is also used as the exterior portion, temperature increase of a portion to be grasped by a user or the like (grasping portion) can be prevented.

Especially in this embodiment, in the main case 20 and the rear case 22 configuring the airtight case 17, only the rear case 22 is partially covered by the rear external cover 60, and heat transfer is executed from the heat transfer sheet 46 to the spring member 70 at the tapered wall portion 22a of the rear case 22 covered by the rear external cover 60, which prevents heat transfer to the side of the main case 20. Consequently, a function of the grasping portion can be achieved without covering the main case 20 by the exterior portion, so that the camera head 3 can be efficiently downsized.

Additionally, the present invention is not limited to each embodiment as described above, and various variations or modifications can be implemented. These variations and modifications are also within the technical scope of the present invention.

What is claimed is:
1. A medical image pickup apparatus comprising:
an enclosed airtight case;
a heat source provided inside the case;
a first heat transfer material arranged inside the case and configured to conduct heat generated by the heat source to an inner surface of the case;
a heat dissipation material arranged outside the case on an outer surface of the case, the inner surface and the outer surface being only separated by a thickness of the case; and
a second heat transfer material arranged outside the case and interposed between the outer surface of the case and the heat dissipation material to conduct heat from the outer surface to the heat dissipation material;
wherein the outer surface corresponds to the inner surface such that the heat conducted to the inner surface of the case is conducted from the inner surface to a corresponding portion of the outer surface of the case across the thickness of the case and is dissipated from the corresponding portion of the outer surface by the heat dissipation material.
2. The medical image pickup apparatus according to claim 1, wherein the second heat transfer material is a spring member pressed to be interposed between the corresponding portion of the outer surface and the heat dissipation material, and elastically contacts the corresponding portion of the outer surface.

3. The medical image pickup apparatus according to claim 1, wherein:
the heat source includes an image pickup device,
the airtight case is formed of one of titanium or titanium alloy,
the first heat transfer material is formed of a sheet-like heat transfer material, and
the second heat transfer material is a leaf spring.

4. The medical image pickup apparatus according to claim 1, wherein the case includes a grasping portion configured to be grasped by an operator on an outer peripheral surface.

5. The medical image pickup apparatus according to claim 1, wherein the second heat transfer material is formed of a material with a higher thermal conductivity than a thermal conductivity of the case.

6. The medical image pickup apparatus according to claim 1, wherein the first heat transfer material is configured to face the second heat transfer material in a longitudinal direction of the case.

7. The medical image pickup apparatus according to claim 1, wherein the second heat transfer material is formed having a ring shape.

8. The medial image pickup apparatus according to claim 1, wherein the heat dissipation material is formed having a ring shape.

9. The medial image pickup apparatus according to claim 1, wherein the first heat transfer material and the second heat transfer material are disposed at a proximal end side of the case.

10. A camera head for use in an endoscope, the camera head comprising:
a case;
a heat source provided inside the case;
a first heat transfer material arranged inside the case and configured to conduct heat generated by the heat source to an inner surface of the case;
a heat dissipation material arranged outside the case on an outer surface of the case, the inner surface and the outer surface being only separated by a thickness of the case; and
a second heat transfer material arranged outside the case and interposed between the outer surface of the case and the heat dissipation material to conduct heat from the outer surface to the heat dissipation material;
wherein the outer surface corresponds to the inner surface such that the heat conducted to the inner surface of the case is conducted from the inner surface to a corresponding portion of the outer surface of the case across the thickness of the case and is dissipated from the corresponding portion of the outer surface by the heat dissipation material.

11. The camera head according to claim 10, wherein the case is configured as an enclosed airtight case.

12. The camera head according to claim 10, wherein the second heat transfer material is a spring member pressed to be interposed between the corresponding portion of the outer surface and the heat dissipation material, and elastically contacts the corresponding portion of the outer surface.

13. The camera head according to claim 10, wherein:
the heat source includes an image pickup device,
the airtight case is formed of one of titanium or titanium alloy,
the first heat transfer material is formed of a sheet-like heat transfer material, and
the second heat transfer material is a leaf spring.

14. The camera head according to claim 10, wherein the case includes a grasping portion configured to be grasped by an operator on an outer peripheral surface.

15. An endoscope system comprising:
a camera head comprising:
a case;
a heat source provided inside the case;
a first heat transfer material arranged inside the case and configured to conduct heat generated by the heat source to an inner surface of the case;
a heat dissipation material arranged outside the case on an outer surface of the case, the inner surface and the outer surface being only separated by a thickness of the case; and
a second heat transfer material arranged outside the case and interposed between the outer surface of the case and the heat dissipation material to conduct heat from the outer surface to the heat dissipation material;
wherein the outer surface corresponds to the inner surface such that the heat conducted to the inner surface of the case is conducted from the inner surface to a corresponding portion of the outer surface of the case across the thickness of the case and is dissipated from the corresponding portion of the outer surface by the heat dissipation material.

16. The endoscope system according to claim 15, wherein the case is configured as an enclosed airtight case.

17. The endoscope system according to claim 15, wherein the second heat transfer material is a spring member pressed to be interposed between the corresponding portion of the outer surface and the heat dissipation material, and elastically contacts the corresponding portion of the outer surface.

18. The endoscope system according to claim 15, wherein:
the heat source includes an image pickup device,
the airtight case is formed of one of titanium or titanium alloy,
the first heat transfer material is formed of a sheet-like heat transfer material, and
the second heat transfer material is a leaf spring.

19. The endoscope system according to claim 15, wherein the case includes a grasping portion configured to be grasped by an operator on an outer peripheral surface.

20. The medical image pickup apparatus according to claim 6, wherein the heat dissipation material and the second heat transfer material are disposed in the longitudinal direction.

* * * * *